United States Patent
Ten Kate et al.

(10) Patent No.: US 10,736,541 B2
(45) Date of Patent: Aug. 11, 2020

(54) MONITORING LIQUID AND/OR FOOD CONSUMPTION OF A PERSON

(71) Applicant: KONINKLIJKE PHILIPS N.V., Eindhoven (NL)

(72) Inventors: Warner Rudolph Theophile Ten Kate, Waalre (NL); Francesco Sartor, Eindhoven (NL); Gabriele Papini, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 255 days.

(21) Appl. No.: 15/565,549

(22) PCT Filed: Mar. 24, 2016

(86) PCT No.: PCT/EP2016/056476
§ 371 (c)(1),
(2) Date: Oct. 10, 2017

(87) PCT Pub. No.: WO2016/162216
PCT Pub. Date: Oct. 13, 2016

(65) Prior Publication Data
US 2018/0116553 A1 May 3, 2018

(30) Foreign Application Priority Data
Apr. 10, 2015 (EP) .................................. 15163083

(51) Int. Cl.
*G01G 19/44* (2006.01)
*G01G 19/50* (2006.01)
*G01G 23/37* (2006.01)
*A61B 5/20* (2006.01)
*G06F 19/00* (2018.01)
(Continued)

(52) U.S. Cl.
CPC .............. *A61B 5/083* (2013.01); *A23L 33/30* (2016.08); *A61B 5/486* (2013.01); *A61B 5/4866* (2013.01); *A61B 5/6887* (2013.01); *A61B 5/743* (2013.01); *A61B 5/746* (2013.01); *G01G 19/44* (2013.01); *G06F 19/3475* (2013.01)

(58) Field of Classification Search
CPC ...... A61B 5/083; A61B 5/4866; G01G 19/44; G01G 19/50; G01G 23/3735
See application file for complete search history.

(56) References Cited

U.S. PATENT DOCUMENTS 2,057,024 A * 10/1936 Gunnison .............. G01G 19/44
177/144
4,697,656 A * 10/1987 de Canecaude ....... G01G 19/44
177/144
(Continued)

FOREIGN PATENT DOCUMENTS

JP 11271136 A 10/1999
JP 2000201858 A 7/2000
(Continued)

*Primary Examiner* — Randy W Gibson

(57) ABSTRACT

Presented are concepts for monitoring the liquid or food consumption of a person. Once such concept employs the step of detecting a change in weight of the person resultant from usage of a toilet. A value representative of at least one of liquid consumption and food consumption of the person may then be determined based on the detected change in weight of the person.

22 Claims, 8 Drawing Sheets

(51) Int. Cl.
    *A61B 5/083*     (2006.01)
    *A61B 5/00*     (2006.01)
    *A23L 33/00*     (2016.01)

(56) References Cited

U.S. PATENT DOCUMENTS

| | | | |
|---|---|---|---|
| 6,038,465 A * | 3/2000 | Melton, Jr. | A61B 5/1171 |
| | | | 600/407 |
| 7,851,711 B2 | 12/2010 | Rump | |
| 9,595,185 B1 * | 3/2017 | Hall | E03D 5/10 |
| 2005/0194192 A1 * | 9/2005 | Kriger | G01G 19/4142 |
| | | | 177/25.19 |
| 2014/0222454 A1 | 8/2014 | Duffy et al. | |
| 2016/0374619 A1 * | 12/2016 | Borkholder | A61B 5/6891 |
| | | | 600/301 |

FOREIGN PATENT DOCUMENTS

| | | |
|---|---|---|
| JP | 2010229648 A | 10/2010 |
| JP | 2011107768 A | 6/2011 |
| KR | 2010030427 A | 3/2010 |
| KR | 2013027329 A | 3/2013 |

\* cited by examiner

MONITORING LIQUID AND/OR FOOD CONSUMPTION OF A PERSON

CROSS-REFERENCE TO PRIOR APPLICATIONS

This application is the U.S. National Phase application under 35 U.S.C. § 371 of International Application No. PCT/EP2016/056476 filed on Mar. 24, 2016, which claims the benefit of European Patent Application No. 15163083.7, filed on Apr. 10, 2015. These applications are hereby incorporated by reference in their entirety herein.

FIELD OF THE INVENTION

This invention relates to a method of monitoring liquid and/or food consumption of a person.

The invention further relates to computer program product for implementing the method and systems for performing the method.

BACKGROUND OF THE INVENTION

Functional assessment or monitoring of a person's health status, physical abilities, mental abilities, or recuperation after injury, hospitalization and treatment is of primary concern in most branches of medicine, including geriatrics, rehabilitation and physical therapy, neurology and orthopaedics, nursing and elder care.

Investigations have found that an individual's functional ability is actually environment-specific, since function increases when subjects are in familiar surroundings due to reduced confusion. Also, one-time assessment of function does not allow for assessment of variability of functional performance over the course of a day or several days, nor does it allow for assessment of change which is important in determining the adequacy of certain clinical services and treatments (such as rehabilitation) following functional loss.

A consensus therefore exists that it is preferable to assess or monitor independent functioning of a person at their home or within familiar surroundings.

A level of independent function is commonly indicated by the quality in which Activities of Daily Living (ADLs) are performed. ADLs refer to the most common activities that people perform during a day. Therefore, a reduced quality in the ADLs can be an indicator for care needed. For example, an anomaly in the regular performance of one or more ADLs can serve as warning for special attention.

Devices and systems have been developed to monitor the ADLs of individuals as they live independently in their own home or within familiar surroundings. For example, one such known system for detecting activities of daily living of a person system comprises three main components: (i) a sensor system that collects information about the person's activities and behaviours; (ii) an intelligence (or information processing) system that interprets the sensor signals for determination of ADL behaviour; and (iii) a user interface system that enables care givers to inspect the interpreted (processed) information. The intelligence system typically makes use of computational techniques known in the art as artificial intelligence. The system may be supported by conventional technologies for data collection, transmission, and storage.

In practice, however, a major difficulty is encountered by the wide range of variations that can happen in actual care cases. Since there are so many possible circumstances, situations and contexts that can occur in daily life, it is common to employ numerous sensors in an attempt to capture enough information about a person's activities to enable identification of specific activities.

The ever-increasing complexity in striving to cover all possible contexts and situations requires more elaborate and detailed information to be collected, processed, interpreted and/or communicated.

Furthermore, scenarios can result in sensor signals that are indicative of an activity, such as eating/drinking for example, even though the activity has not been undertaken. Thus, despite being complex and costly, conventional ADL monitoring concepts can exhibit low accuracy. This is particularly the case for the ADL of eating/drinking because there are lots of scenarios that may be indicative of a monitored person eating/drinking whilst not actually guaranteeing that the person has indeed consumed liquid and/or food.

SUMMARY OF THE INVENTION

The invention aims to at least partly fulfil the aforementioned needs. To this end, the invention provides systems and methods as defined in the independent claims. The dependent claims provide advantageous embodiments.

Proposed is the concept of inferring the liquid and/or food consumption of a person from their change in weight that results from their use of a toilet. Put another way, determination of liquid or food consumption of a person may be based on the weight of their excretions. By detecting a person's change in weight resultant from a single visit to the toilet, the weight of excreted matter may be inferred and, from this, food/liquid consumption may be determined. Thus, there is proposed the concept of measuring the weight loss of a person resulting from a toilet visit. The measured weight loss may be used to infer liquid or food consumption of the person, and this may be undertaken in relation to numerous toilet visits so as to enable monitoring of the person's liquid or food consumption over time. Furthermore, previously determined values (e.g. cumulative weight losses) for a predetermined timeframe (e.g. a day) may be used to estimate food and/or liquid consumption of a current and/or preceding timeframe. In other words, weight measurements can be indicative of consumption that has occurred previously, and time delays/differences between consumption and weight measurement(s) may depend on the type of food or liquid consumed (due to digestion properties, for example).

The value representative of the change in weight of a person as a result of the persons use of the toilet is related to the weight of the person before and after a single usage of the toilet (10) and this can be determined from detecting the change in weight of the person based on the detected weight of the person before and after the single usage of the toilet.

The processing device is able to obtain (e.g. receive) a value representative of the change in weight, or is able to provide such value form other data related to weight change of a person resultant from a toilet visit. The latter data can be raw weight data of a person before and after the toilet visit. Preferably such latter data are obtained within 1 hour before or 1 hour after the toilet visit, but more preferably, such time periods before and after the toilet visit are individually or both less than 30 minutes, less than 15 minutes, less than 5 minutes, less than 1 minute.

Liquid or food consumption of a person may therefore be inferred at a single location (e.g. a toilet) using a single sensor (e.g. weight scale). This may help to reduce associated cost and/or complexity of an ADL monitoring system. For example, conventional ADL monitoring systems may be adapted to detect or monitor eating and drinking by employing sensors installed on a refrigerator (e.g. an open-close sensor), sensors installed in cupboards/drawers holding cutlery/food, power sensors on cooking equipment, presence sensors for detecting a user's presence in kitchen; a pressure sensor installed in a seat of a dining table, etc. Conversely, embodiments may avoid the need for multiple sensors (and complex signal processing of their respective signals) and may instead simply employ a single weight sensing arrangement.

The method and system can be for monitoring activities of daily living. Activities of daily living concern basic activities that a person executes on a regular basis. Examples of activities of daily living are drinking/eating; cooking; medicating; sleeping; toileting; bathing; washing, any kind of exercising such as walking, leisure activities such as reading or TV watching and many more etc. Thus, the invention may provide a way to monitor the ADL of drinking/eating in a simple and easy to implement manner.

The method, system or data processing unit may be adapted to determine a value representative of at least one of liquid consumption and food consumption of the person further based on at least one of: a value representative of weight lost by perspiration of the person; a value representative of weight lost by respiration of the person; a value representative of reference weight; one or more previously detected values of weight of the person; one or more previously detected changes in weight of the person; and one or more previously determined values representative of preceding liquid or food consumption of the person.

The reference weight can be determined once or periodically and stored for use in the method and system. The reference weight can be an average weight determined over time.

Thus, previously determined values representative of liquid or food consumption of the person may therefore be stored, in a database for example, and then used in subsequent calculations. Furthermore, currently calculated values representative of liquid or food consumption may be used to re-calculate or refine previously determined values representative of liquid or food consumption (e.g. those stored in database for example).

In the method or the system, the value representative of the at least one of the liquid consumption and the food consumption of the person is equal to, or is further based on the sum of:

the current value of representative of the change in weight of the person;

the value representative of the reference weight;

the value representative of weight lost by perspiration of the person

If the value is further based on these sum terms, other terms or factors can be used for further refinement of the value.

Alternatively, the value Win representative of at least one of liquid consumption and food consumption of the person is thus obtained as: $W_{in}=W_{st}+W_{ex}+W_{il}$, wherein $W_{st}$ is a value representative of weight stored by the person, $W_{ex}$ is the determined change in weight of the person, and $W_{il}$ is a value representative of weight lost by perspiration of the person.

The weight sensing system may be adapted to detect the weight of the person before and after a single usage of the toilet and to determine the change in weight of the person based on the detected weight of the person before and after the single usage of the toilet.

The method and system or the data processing unit may be adapted to be able to compare the determined value representative of at least one of liquid consumption and food consumption with a threshold value and to generate a warning signal if the determined value exceeds the first threshold value. The threshold can be preprogramed and fixed, but is preferably also enabled to be set by a user preference. Further, the threshold may be based on previously determined values representative of liquid/food consumption of the person. The threshold may be based on at least one of: one or more previously detected changes in weight of the person; and one or more previously detected values of weight of the person. In other words, the threshold may be defined by taking account of a history of detected values and/or a history of liquid/food consumption of the person so that it can be used to identify outlying values or anomalies (using trend analysis, for example).

Also, the threshold may be enabled to be set to act on a person to be monitored or act on a group of persons to be monitored.

The method, system or data processing unit may be further adapted to generate a control signal for modifying a graphical element based on the determined value representative of at least one of liquid consumption and food consumption of the person. Further, the ADL monitoring system may further comprise a display system adapted to display the graphical element in accordance with the control signal generated by the data processing unit. In this way, a user (such as a care giver) may have an appropriately arranged display system that can receive and display information about the ADL of eating or drinking of a person, and that person may be remotely located from the user. Embodiments may therefore enable a user to remotely monitor the liquid or food consumption of a person using a portable display device, such as a laptop, tablet computer, mobile phone, PDA, etc.

The data processing unit may be remotely located from the weight sensing system, and a signal representative of the determined change in weight of the person may be communicated to the data processing unit via a communication link. The communication link can be any known communication link for wired and/or wireless communication of data. It may be a secured communication link.

Thus, it will be understood that processing capabilities may therefore be distributed throughout the system in different ways according to predetermined constraints and/or availability of processing resources.

The system may comprise a server device comprising the data processing unit and a communication link; the server device being capable of communication through the communication link with a client device which device may or may not include the weight sensing system. The client device can be part of the system, but this is not needed. In these cases the server device is able to obtain the relevant data relating to the weight change of the person when he has used the toilet. From these data the server determines the food and/or liquid consumption. The relevant data can e.g. be raw weight data or can be pre-processed data in the form of the value representative of the weight as described with respect to the main independent claim herein before. Such setup can enable central data processing for a multitude of data sources (clients). Thus, the data can come from multiple toilets in one home, or multiple toilets in multiple homes to be processed in one server with one or more (distributed) data processors. This can keep clients simple and cheap.

Alternatively, the system may comprise a client device comprising the data processing unit and a communication link; the client device being capable of communication through the communication link with a server device. The server device can be part of the system, but this is not needed. In these cases the client device is able to obtain the relevant data relating to the weight change of the person when he has used the toilet. From these data it determined the food and/or liquid consumption. The relevant data can e.g. be raw weight data or can be pre-processed data in the form of the value representative of the weight as described with respect to the main independent claim herein before. The client device can include the weight sensing system, but this is not needed. Such setup is advantageous for using available computing power locally. Also not all data need to be transmitted to the server. It may be only the final food and/or liquid consumption data that are transmitted to the server or any other device for display of such data.

Dedicated data processing means may therefore be employed for the purpose of determining a value representative of at least one of liquid consumption and food consumption of the person, thus reducing processing requirements or capabilities of other components or devices of the system.

The system may further comprise a display system. In other words, a user (such as a care giver) may have an appropriately arranged client device (such as a laptop, tablet computer, mobile phone, PDA, etc.) which processes received data in order to determine a value representative of at least one of liquid consumption and food consumption of the person.

The weight sensing system may be positioned in the toilet itself for measuring the weight of the person before and after usage. There is the risk of a person not sitting down for his particular toilet visit. An important monitoring opportunity may be lost in that case. Therefore, in a preferred weight sensing system is positioned in front of the toilet so that it is stood on by the person before and after the person's usage of the toilet. In this way, a person need only undertake their normal activities when using the toilet. Such positioning may ensure that a change in weight of the person can be automatically and accurately obtained for each single usage of the toilet (e.g. every time the person uses the toilet), and this may not require the person to remember to undertake any special or additional activities in order for a change in weight determination to be made. This may remove the risk of the person forgetting to activate a weight sensing system (e.g. by pressing a button), for example.

There exist many sensors that can be employed by an ADL monitoring system. Typical sensors include PIR (Passive Infra-Red; measure movement and presence), OC (open-close; measure state of doors, in particular front doors, windows, and cupboards, including refrigerators), power sensors (measure current consumption of appliances, such as microwave, water cookers, TV, etc), and pressure mats (measure occupancy of user sitting in chair, lying in bed, standing on door mat in front of front door, etc). Many others exist and are conceivable, such as sensors to signal light switch state, or sensors that measure environmental conditions such as humidity, CO2 level (or CO and smoke), Particulate Matter level, etc. A further range of sensors are those based on physical quantities, such as accelerometers, magnetometers, gyroscopes, and air pressure sensors. Accelerometers, for example, can also measure state of doors and their open-close movements. Yet another range of sensors consists of microphones and cameras (including infra-red, or even UV and beyond, part of spectrum), to which also belong GPS and location-sensitive IR. Ultra-sound or RF-based sensors, including RFID tagging, provide additional input. Appliances having an own IP-address, known as the internet-of-things, provide further sensor input signals that can be taken by the smart-home system.

Although the sensor(s) may be mounted in the environment (e.g. the person's home), they may also be attached to user utilities (such as a keyring) or put in clothes, in a pocket or bag, or as insole or undergarment, etc. They may also be fabricated to be worn explicitly like a wrist watch or pendant. Further, the sensors may communicate their output signals via a wired or wireless connection, or a combination thereof.

The sensors may also be adapted to undertake primary processing of the detected values, such a signal filtering, sampling, conditioning, etc., so as to reduce required transmission bandwidth and/or transmission duration for example. Alternatively, the sensors can send raw data.

Non-intrusive monitoring may therefore be realized with relative simple sensors that provide data on specific ambient conditions or properties/parameters of the environment (such as temperature or humidity for example), or properties of the person (such as movement, for example). Such sensors for measuring ambient condition or properties/parameters of the environment may be simple, small and/or cheap. Also, the movement of the person may be detected with, for example, a Passive InfraRed (PIR) sensor which is a cheap component. Movement sensors may be used to switch on lighting and people are therefore typically familiar with their usage.

Thus, ADL monitoring systems of the invention may employ such sensors that are considered to be non-intrusive and more easily accepted by the monitored person. Yet, with the data provided by these sensors, ADLs may be determined and provide information on the person being monitored.

Such sensors may be employed by, or in conjunction with, the weight sensing system so as to increase the number and/or accuracy of monitored ADLs. They may also be used to confirm or qualify readings taken by the weight sensing system, so that spurious or unintentional measurements are avoided. For example, signals from a location sensor worn by the monitored person may be used to confirm if weight readings taken by the weight sensing system are indeed attributable to the monitored person or some other person or animal (such as their pet), for example.

There is provided a method for monitoring the liquid or food consumption of a person, wherein the method comprises: determining a change in weight of the person resultant from usage of a toilet; and determining a value representative of at least one of liquid consumption and food consumption of the person based on the detected change in weight of the person.

The step of determining a value representative of at least one of liquid consumption and food consumption of the person may be further based on at least one of: a value representative of weight lost by perspiration of the person; a value representative of weight lost by respiration of the person; a value representative of weight stored by the person; one or more previously detected values of weight of the person; one or more previously detected changes in weight of the person; and one or more previously determined values representative of preceding liquid or food consumption of the person.

The step of determining a change in weight of the person may comprise: detecting the weight of the person before and after a single usage of the toilet; and determining the change in weight of the person based on the detected weight of the person before and after the single usage of the toilet.

The method may further comprise: comparing the determined value representative of at least one of liquid consumption and food consumption with a threshold value; and generating a warning signal based on the comparison result.

The method may further comprise the preceding step of: further comprising the preceding step of: determining the threshold value based on at least one of: one or more previously determined values representative of preceding liquid or food consumption of the person; one or more previously detected changes in weight of the person; and one or more previously detected values of weight of the person.

There is provided a computer program product for monitoring the liquid or food consumption of a person, wherein the computer program product comprises a computer-readable storage medium having computer-readable program code embodied therewith, the computer-readable program code configured to perform all of the steps of an embodiment.

A computer system may be provided which comprises: a computer program product according to an embodiment; and one or more processors adapted to perform a method according to an embodiment by execution of the computer-readable program code of said computer program product.

In a further aspect the invention relates to a computer-readable non-transitory storage medium comprising instructions which, when executed by a processing device, execute the steps of the method of controlling an ADL monitoring system display unit according to an embodiment.

These and other aspects of the invention will be apparent from and elucidated with reference to the embodiment(s) described hereinafter.

BRIEF DESCRIPTION OF THE DRAWINGS

Examples in accordance with aspects of the invention will now be described in detail with reference to the accompanying schematic drawings, in which.

DETAILED DESCRIPTION OF THE EMBODIMENTS

Figure 1:
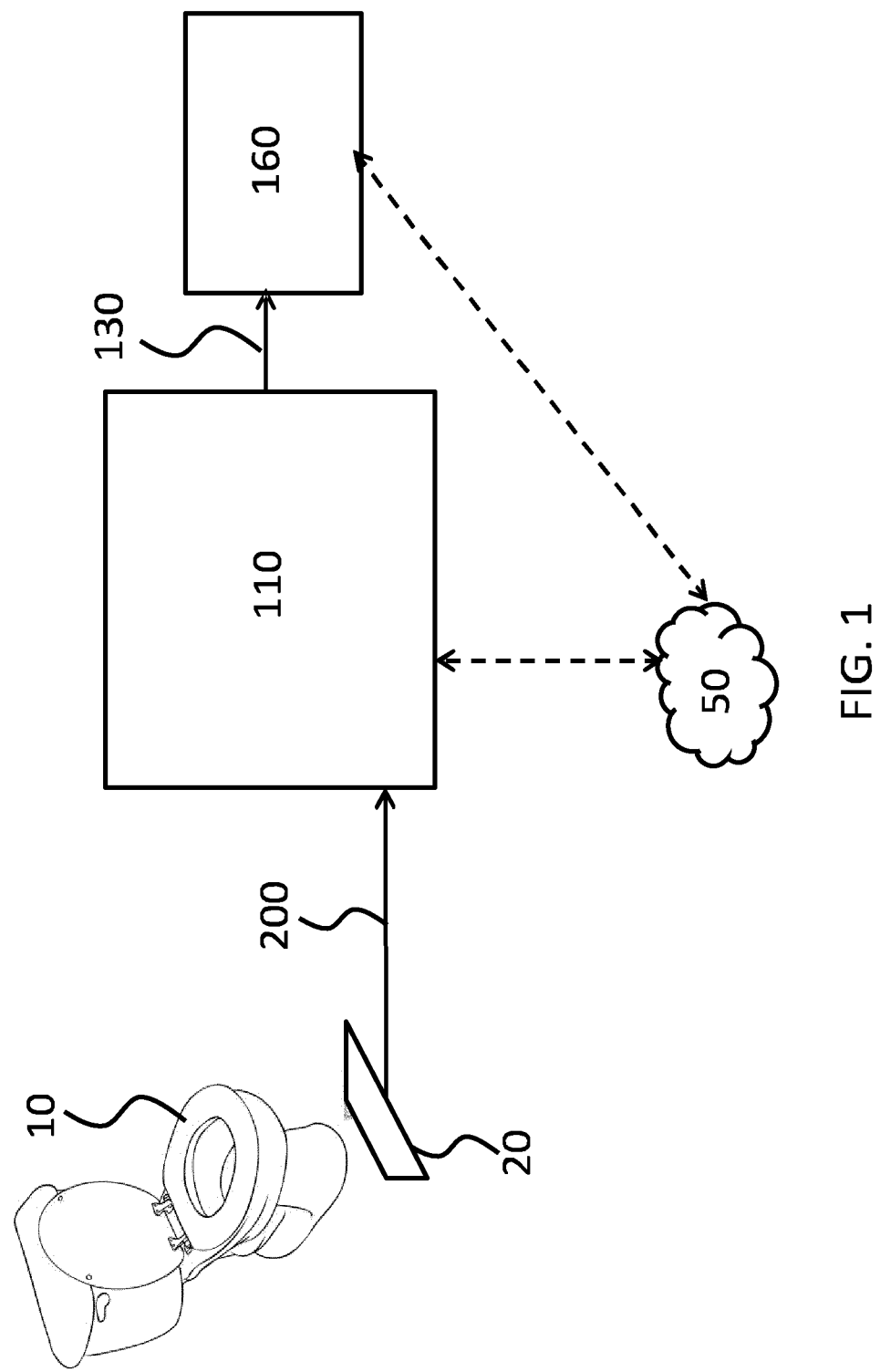
FIG. 1 is a simplified block diagram of a system for monitoring the liquid or food consumption of a person according to an embodiment.

Proposed is a concept for inferring the liquid or food consumption of a person, which may be useful for the purpose of monitoring ADLs of the person for example. Such persons may, for example, include a disabled person, an elderly person, an injured person, a medical patient, etc. Elderly persons can mean persons above 65 years, above 70, or above 80 years old.

Illustrative embodiments may be utilized in many different types of monitoring environments, such as a hospital, ward, care home, person's home, etc. In order to provide a context for the description of elements and functionality of the illustrative embodiments, the Figures are provided hereafter as examples of how aspects of the illustrative embodiments may be implemented. It should therefore be appreciated the Figures are only examples and are not intended to assert or imply any limitation with regard to the environments, systems or methods in which aspects or embodiments of the present invention may be implemented.

In general, to be able to observe changes in "normal" daily behavior of a person one may monitor ADLs of a person spot unexpected activities, anomalies or deviations from expected patterns. The type of anomaly or irregularity can be different per case.

A large class of anomalies relate to aberrations in an ADL routine of the person. For example, an above average number of toilet visits during the night.

By way of example, ADLs may include:
(i) Medication
  a. Is the elder taking his medicine in proper way at proper moments?
  b. Is the elder taking the correct/prescribed medication?
(ii) Sleep
  a. Is the elder sleeping sufficiently and undisturbed?
(iii) Eating/Drinking
  a. Is the elder eating sufficiently and regularly?
  b. Does he prepare meals by himself?
(iv) Physical activity
  a. Is the elder active during the day?
  b. Is there little sedentary behaviour?
(v) Toileting
  a. Is the elder toileting in normal way?
  b. Are there frequent visits to the toilet during the night?
(vi) Bathing
  a. Is the elder bathing adequately?
(vii) Being In/Out House
  a. Is the elder going out?
(xiii) Ambient climate
  a. Is the environment "clean"?
  b. E.g., is temperature proper, is the $CO_2$ level healthy, is the particle (PM) level healthy?
(ix) Etc.

Based on the above exemplary ADLs, the following examples of anomalies, irregularities or warnings may relate to:

A. Sign of activity, or sign of inactivity
B. Presence in rooms considered risky (e.g. alone in kitchen when elder is suffering dementia)
C. Leaving the house at unexpected moments, such as during the night D. Exceptional frequency or exceptional duration of toilet visits E. Exceptional duration of bathing F. Sleeping shorter G. Reduced activity H. Etc.

Embodiments of the present invention are directed toward enabling information about the liquid or food consumption of a person to be obtained and potentially monitored. Such information may therefore be useful for monitoring ADLs of the person, such as eating/drinking, physical activity and toileting, for example.

Embodiments employ the concept of inferring the liquid or food consumption of a person from their change in weight when they use a toilet. In other words, determination of liquid or food consumption of a person may be based on the weight of their excretions. Measured weight loss resulting from a toilet visit may therefore be used to infer liquid or food consumption of the person, and this may be undertaken in relation to numerous toilet visits so as to enable monitoring of the person's liquid or food consumption over time.

Liquid or food consumption of a person can therefore be inferred using a single sensor (e.g. a weight scale) installed at a single location (e.g. a toilet), thus reducing the burden, cost and/or complexity of a system according to an embodiment. It may also help to ensure toilet visits are accurately detected, thus improving the accuracy of monitoring results. Such a proposed concept for inferring liquid or food consumption of a person may therefore be employed in a system for monitoring ADLs of a person within an environment.

ADL events may be detected or inferred from sensor output signals and there already exist systems and methods for such ADL detection or inference. Accordingly, the proposed concepts may be used in conjunction with existing ADL detection or monitoring systems/methods. For example, Dries Vermeiren et al describe a system based on 2 tri-axial accelerometers to detect the ADLs of a patient in a paper entitled "Detecting Human Motion: Introducing Step, Fall and ADL algorithms". Also, H Pirsiavas et al describe algorithms for detecting ADLs in first-person camera views in paper entitled "Detecting activities of daily living in first-person camera views" (CVPR, 2012). Because many such ADL detection or monitoring methods/systems are known and any one or more of these may be employed, detailed description of such methods/systems is omitted from this description.

FIG. 1 shows an embodiment of a system according to the invention comprising a toilet 10 and weight sensor 20 adapted to determine a change in weight of a person which results from the person's usage of the toilet 10.

Here, the weight sensor 20 is situated immediately in front of the toilet 10 so that it is stood on by the person before and after the person uses the toilet 10. For example, the weight sensor may be integrated into flooring which surrounds the front of the toilet 10. In this way, a person need only undertake their normal activities when using the toilet and may not even be aware that they are standing on a weight sensor and being weighed. Such positioning (in close proximity to the toilet 10, for example) may ensure that a change in weight of the person can be automatically and accurately obtained for each single usage of the toilet (e.g. every time the person uses the toilet) without requiring the person to remember to undertake any special or additional activities in order for a change in weight determination to be made. For example, it can remove the need for a person to perform a specific additional action (e.g. pressing a button) in order to activate the weight sensor 20.

The weight sensor 20 comprises a sensing arrangement that is adapted to determine the weight of a person before and after using the toilet. More specifically, the weight sensor 20 detects a value of a person's weight when they stand on the sensor 20 on front of the toilet. The weight sensor 20 obtains numerous measurements of the person's weight before, during and after the person they use the toilet.

The weight sensor 20 is adapted to output sensor output signals 200 which are representative of the detected value(s) of the person's weight. Of course, many more sensors may be employed so as to provide signals indicative of the environment and/or the person's movement/activities. Such additional signals may be useful for identifying which of the sensor output signals 200 are indicative of the person's weight before and after usage of the toilet. They may also be used to confirm or qualify values detected by the weight sensor 20, so that spurious or unintentional measurements are avoided. For example, signals from a location sensor worn by the monitored person may be used to confirm if weight readings taken by the weight sensor 20 are indeed attributable to the monitored person using the toilet 10, for example.

The weight sensor 20 communicates its output signals 200 via a wired or wireless connection. By way of example, the wireless connection may comprise a short-to-medium-range communication link. For the avoidance of doubt, short-to-medium-range communication link may be taken to mean a short-range or medium-range communication link having a range of up to around 100 meters. In short-range communication links designed for very short communication distances, signals typically travel from a few centimeters to several meters, whereas, in medium-range communication links designed for short to medium communication distances, signals typically travel up to 100 meters. Examples of short-range wireless communication links are ANT+, Bluetooth, Bluetooth low energy, IEEE 802.15.4, ISA100a, Infrared (IrDA), Near Field Communication (NFC), RFID, 6LoWPAN, UWB, Wireless HART, Wireless HD, Wireless USB, ZigBee. Examples of medium-range communication links include Wi-Fi, ISM Band, Z-Wave. Here, the output signals are not encrypted for communication via the wired or wireless connection in a secured manner. However, it will be appreciated that, in other embodiment, one or more encryption techniques and/or one or more secure communication links may be employed for the communication of signals in the system.

The system further comprises a data processing unit 110 adapted to receive the sensor output signals 200, and to determine a value (Win) representative of at least one of liquid consumption and food consumption of the person based on the detected change in weight of the person. For this purpose, the data processing unit 110 may communicate with one or more data processing resources available in the internet or "cloud" 50. Such data processing resources may undertake part or all of the processing required to infer a value (Win) representative of at least one of liquid consumption and food consumption based on the received sensor output signals 200. Thus, the embodiment may employ distributed processing principles.

The data processing unit 110 is further adapted to generate an output signal 130 representative of an inferred or detected value (Win) representative of the liquid and/or food consumption of the person. In other words, after having inferred a value (Win) representative of the liquid and/or food consumption of the based on the received sensor output signals (either with or without communicating with data processing resources via the internet or "cloud"), an output signal 130 representative of the liquid and/or food consumption of the person is generated.

The system further comprises a graphical user interface (GUI) 160 for providing information to one or more users. The output signal 130 is provided to the GUI 160 via wired or wireless connection. By way of example, the wireless connection may comprise a short-to-medium-range communication link. As indicated in FIG. 1, the output signal 130 is provided to the GUI 160 from the data processing unit 110. However, where the system, has made use of data processing resources via the internet or cloud 50), an output signal may be made available to the GUI 160 via the internet or cloud 50.

Based on the output signal 130, the GUI 160 is adapted to communicate information by displaying one or more graphical elements in a display area of the GUI 160. In this way, the system may communicate information about liquid and/or food consumption of the person that may be useful for indicating that the person is in need of attention. For example, the GUI 160 may be used to display graphical elements to a medical practitioner, a caregiver, a family member or close relative. Alternatively, or in addition, the GUI 160 may be adapted to display graphical elements to the monitored person.

Figure 2A:
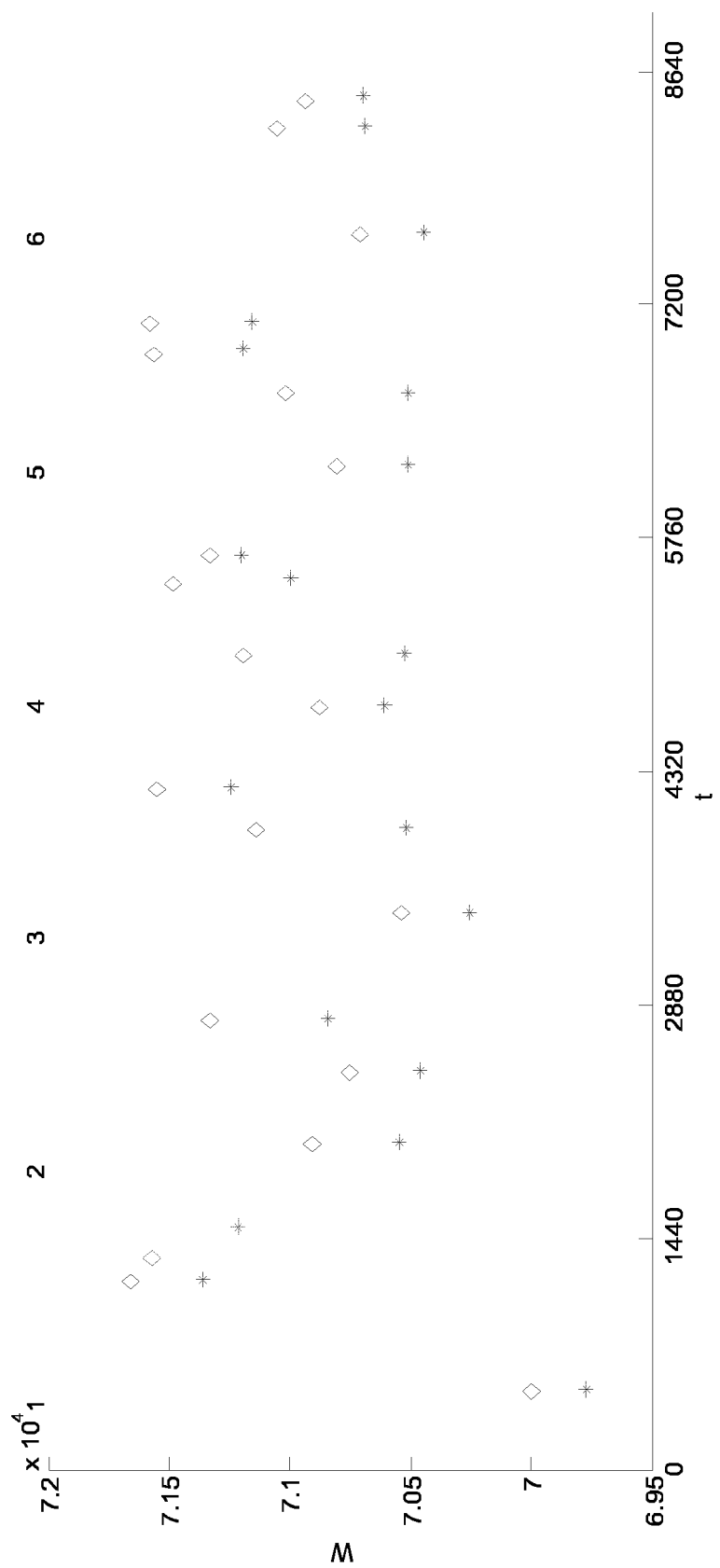
FIG. 2A depicts detected values of a first person's body weight before and after usage of the toiler over the course of six days, wherein the first person is known to have a relatively low level of liquid intake (i.e. a low value of liquid consumption)
Figure 2B:
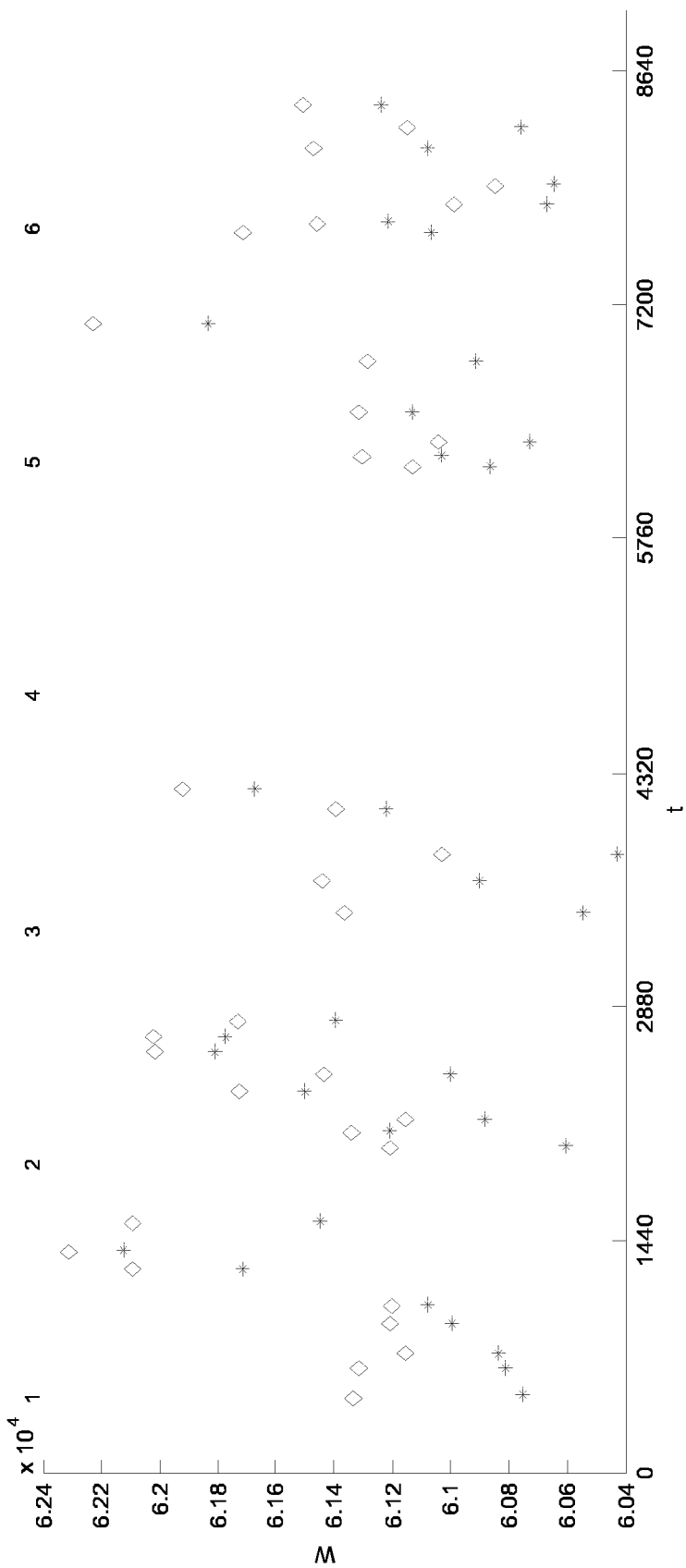
FIG. 2B depicts detected values of a second person's body weight before and after usage of the toiler over the course of six days, wherein the first person is known to have a relatively high level of liquid intake (i.e. a high value of liquid consumption)

Referring now to FIGS. 2A and 2B, example toilet behaviour of two different persons (as detected by the system of FIG. 1) is illustrated using graphs.

The graph of FIG. 2A depicts the detected values of a first person's body weight (W) measured in grams before and after usage of the toilet over a time period (t) of six days. The detected values of pre-toilet weight are indicated using a diamond-shaped identifier "◊", and detected values of post-toilet weight are indicated using a star-shaped identifier "*". The first person is known to have a relatively low level of liquid intake (i.e. a low value of liquid consumption).

The graph of FIG. 2B depicts the detected values of a second person's body weight (W) measure in grams before and after usage of the toilet over the same time period (t) of six days. The detected values of pre-toilet weight are indicated using a diamond-shaped identifier "◊", and detected values of post-toilet weight are indicated using a star-shaped identifier "*". The second person is known to have a relatively high level of liquid intake (i.e. a high value of liquid consumption).

From the graphs of FIGS. 2A and 2B, it can be seen that a person's weight decreases as a direct result of using the toilet. This decrease in bodyweight is assumed to directly relate to the weight of excreted matter.

From the graphs of FIGS. 2A and 2B, it can also be seen that amount by which a person's weight decreases as a direct result of using the toilet is dependent on their liquid intake (e.g. their level of liquid consumption). In particular, it is noted that, for a single toilet visit, the person having a relatively high level of liquid intake typically exhibits a larger decrease/reduction in bodyweight when compared to the person having a relatively low level of liquid intake (i.e. a low value of liquid consumption. This is seen from the typically larger spacing between associated pre-toilet and post-toilet bodyweight values of FIG. 2B.

It has been realised that the change in bodyweight resulting from each toilet visit can be linked to the eating/drinking behaviour of the person during the previous day. Further, the liquid consumption and/or food consumption of the person may be based on other factors including: a value representative of weight lost by perspiration of the person; and a value representative of weight stored by the person.

Using this understanding, the following model/equation (i) can be used to obtain a value Win representative of at least one of liquid consumption and food consumption of the person:

$$Win = Wst + Wex + Wil \qquad (i),$$

wherein: Wst is a value representative of weight stored by the person; Wex is the determined change in weight of the person; and Wil is a value representative of weight lost by perspiration and respiration of the person.

Figure 3:
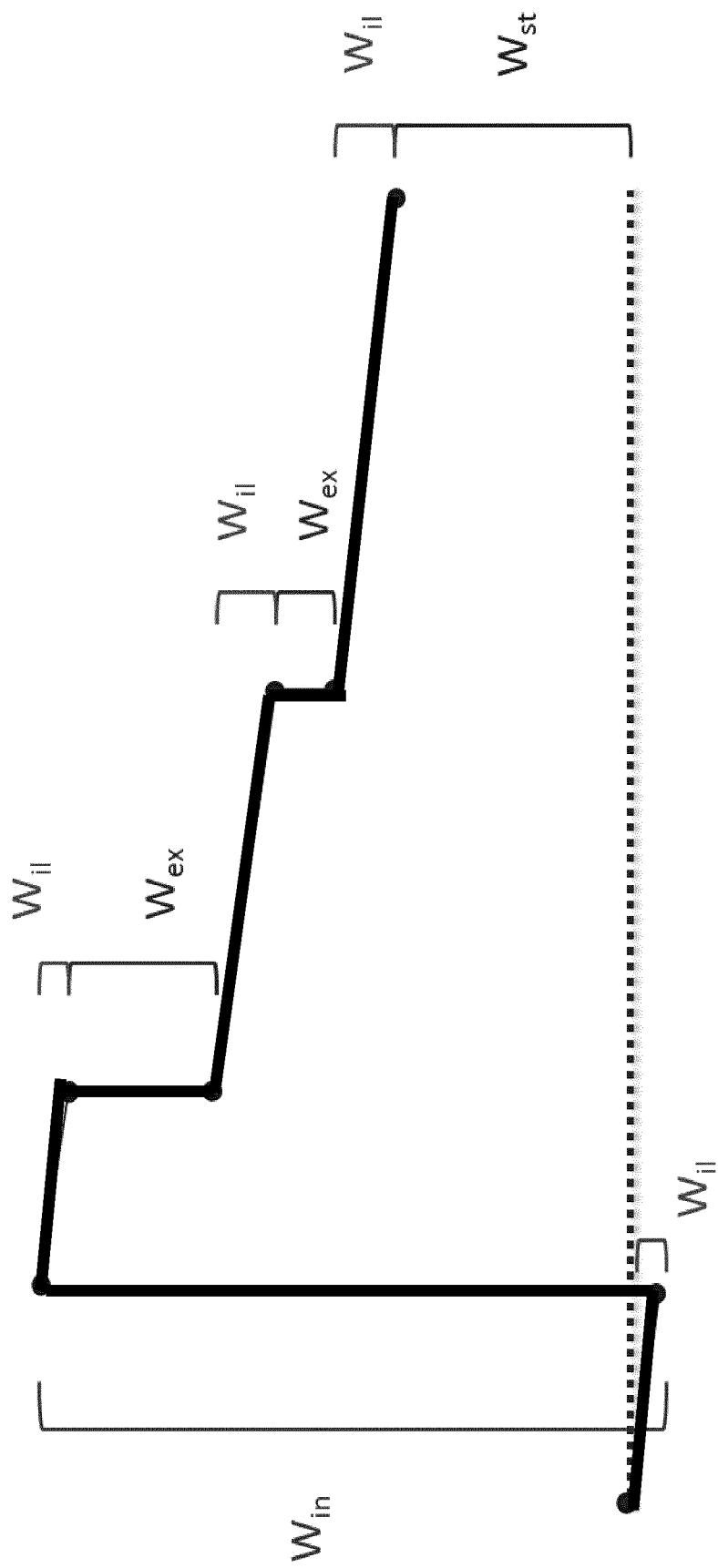
FIG. 3 depicts an exemplary pattern of weight changes for a person over the course of a single day.

For example, referring to FIG. 3, there is depicted an exemplary pattern of weight changes for a person over the course of a single day. The thick/bold line represents he variation of a person's bodyweight due to food/drink intake, toileting and insensible weight loss (due to perspiration for example) and weight storage.

If one considers that the insensible weight loss Wil (due to perspiration, for example) can be taken as a constant that is dependent on body size, and environmental conditions (e.g. temperature and humidity), and that stored weight Wst can be computed by considering the weight changes of the person over three or more days, the value Win representative of liquid/food intake may be assumed to be the main influence of the change Wex in bodyweight. Thus, by measuring Wex (the change in bodyweight resulting from toilet usage), one can infer a value Win representative of at least one of liquid consumption and food consumption of the person.

Figure 4:
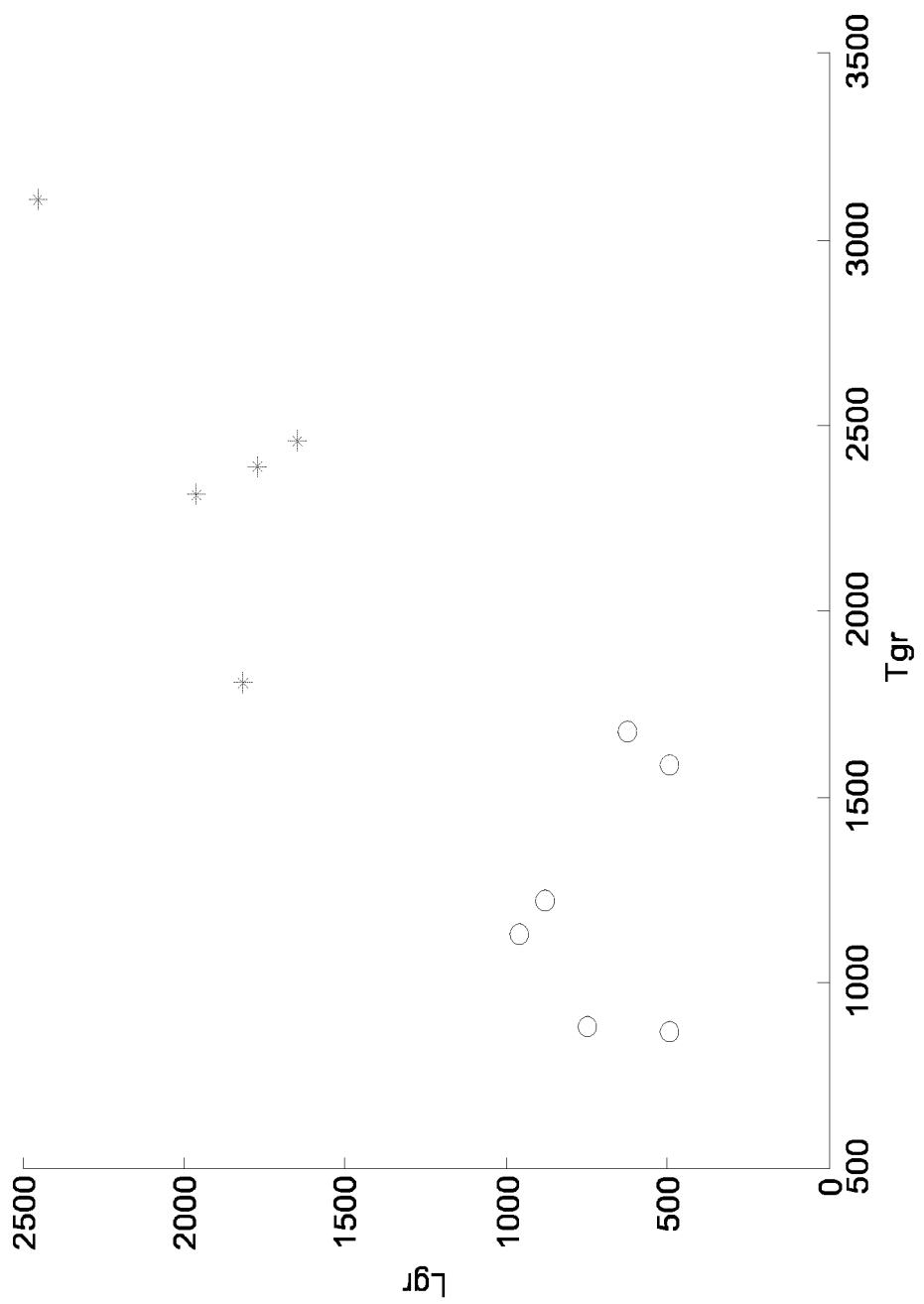
FIG. 4 is a graph of detected values of liquid intake plotted against the detected reduction in bodyweight resulting from a toilet visit for the persons of FIGS. 2A and 2B.

Referring to FIG. 4, there is depicted a graph showing values of liquid intake (measured in grams and denoted "Lgr") plotted against the associated reduction in bodyweight (measure in grams and denoted "Tgr") resulting from a toilet visit for the persons of FIGS. 2A and 2B. Values for the first person are indicated using a star-shaped identifier "*", and values for the second person are indicated using a circle-shaped identifier "○". For the plotted values of FIG. 4, a generally linear correlation is exhibited, wherein the linear correlation coefficient is determined as being 0.87. A strong correlation between (zero calories) liquid intake and excretion is therefore noted, thus supporting the concept that excretion values (e.g. Wex the change in bodyweight resulting from toilet usage) can be used to estimate the liquid and/or food intake of the person that preceded. For example, using regression techniques, recent eating/drinking can be inferred from a detected weight loss resulting from using the toilet. Further, values of detected weight loss may be stored and/or accumulated for a plurality of toilet visits, and such accumulated values may be used for the purpose of improving the accuracy of inferred or calculated values representative of eating/drinking behaviour.

Embodiments may cater for more complex relationships between liquid/food consumption and change in bodyweight resultant from toilet usage by accounting for additional factors or parameters. Such additional factors may account for varying digesting time of different foods, for example, which can result in 'blur' in the weight changes.

Stored weight Wst may therefore be modelled as a combination of future excretion and energy storage. By modelling this, the inverted transfer function can be 'de-blurred', for example, in the form of a Kalman Filter.

Also, previously determined values representative of liquid or food consumption of the person may be stored, in a database for example, and then used in current or subsequent calculations.

Thus, by storing previous detected changes in weight and/or tracking activity levels, temperature, etc. of the person, estimates of excretion due to metabolism and/or body temperature regulation can be compensated for in the data processing process.

Furthermore, currently calculated values representative of liquid or food consumption may be used to re-calculate or refine previously determined values representative of liquid or food consumption (e.g. those stored in database for example).

Figure 5:
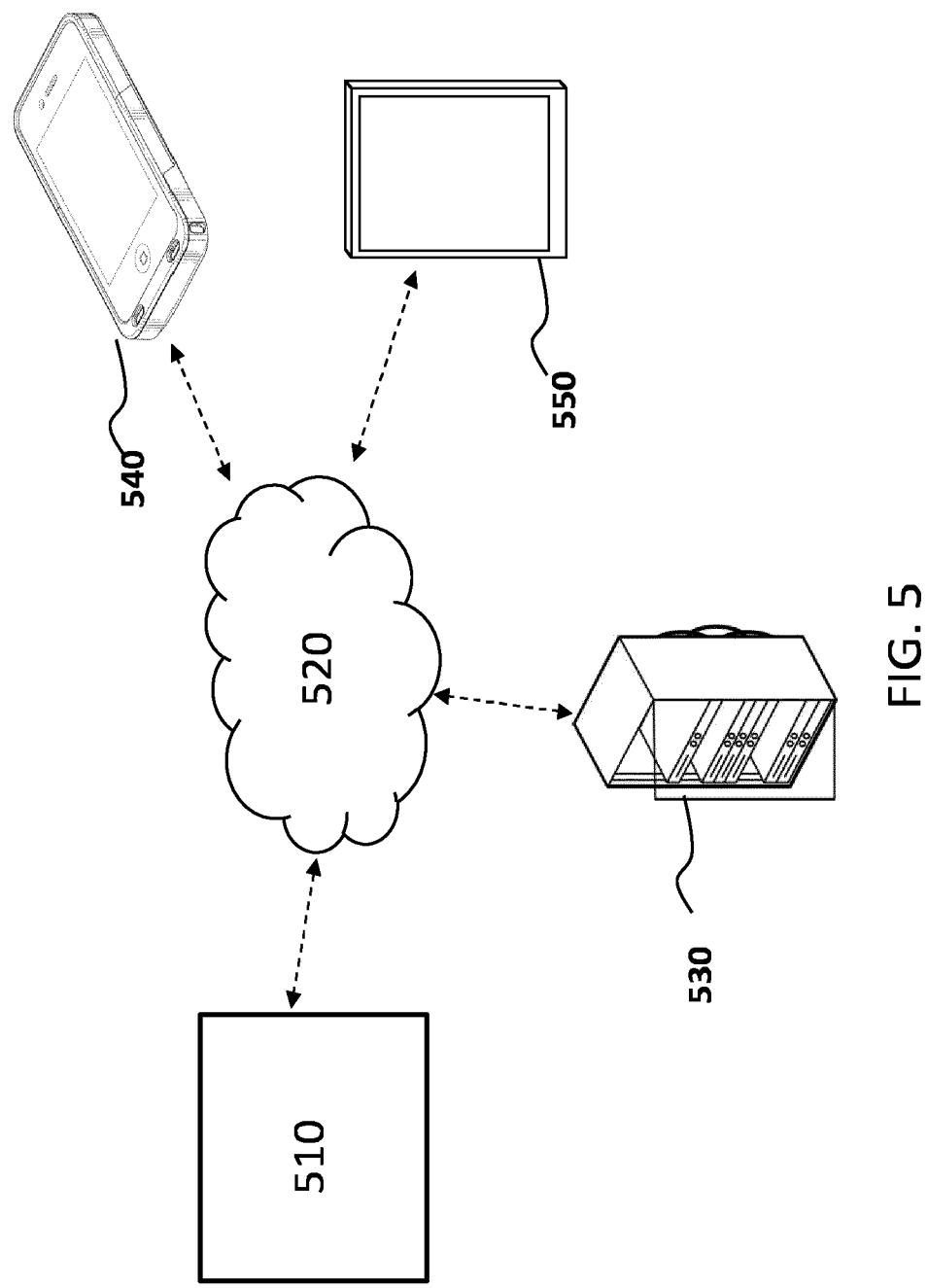
FIG. 5 is a simplified block diagram of a system according to an embodiment.

Referring now to FIG. 5, there is depicted another embodiment of a system according to the invention comprising a weight sensing system 510 adapted to determine a change in weight of the person resultant from usage of a toilet.

Here, the weight sensing system 510 comprises a high-resolution weight scale adapted to be integrated into a toilet (for example, within the toilet seat). The weight sensing system 510 is adapted to output one or more signals which are representative of the detected value(s) of a person's weight at least before and after using the toilet.

Although this embodiment has been described as integrating the weight sensing system 510 into the toilet, it will be understood that, in alternative embodiments, the weight sensing system 510 may be provided separately from the toilet such that it requires a person to be aware of the weight sensing system 510 and actively use the weight sensing system 510 before and after using the toilet. Such an alternative arrangement may avoid the need for additional sensors (to confirm or qualify values detected by the weight sensing system, for example) and thus be more simple and/or cheaper. For example, instead of being integrated into the toilet, the weight sensing system may be positioned at the entrance or doorway leading to the toilet so as to measuring a person's weight upon entering and leaving the room. Further, where multiple toilet locations are provided (e.g. on first and second floors, etc.), multiple weight sensing systems may be employed and the measurements combined.

The weight sensing system 510 communicates the output signals via the Internet 520 (using a wired or wireless connection for example) to a remotely located data processing system 530 (such as server).

The data processing system 530 is adapted to receive the one or more output signals from the weight sensing system 510 and process the received signal(s) in accordance with an inference/detection algorithm in order to infer/determine a value representative of liquid/food consumption of the person based on the determined change in weight of the person. The data processing system 530 is further adapted to generate output signals representative of inferred or detected value representative of liquid/food consumption. Thus, the data processing 530 provides a centrally accessible processing resource that can receive information from the weight sensing system and run one or more algorithms to transform the received information into one or more values representative of liquid/food consumption. Information relating to the one or more values representative of liquid/food consumption can be stored by the data processing system (for example, in a database) and provided to other components of the system. Such provision of information about detected or inferred liquid/food consumption may be undertaken in response to a receiving a request (via the internet 520 for example) and/or may be undertaken without request (i.e. 'pushed').

For the purpose of receiving information about detected or inferred liquid/food consumption from the data processing system, and thus to enable liquid/food consumption to be monitored, the system further comprises first 540 and second 550 mobile computing devices.

Here, the first mobile computing device 540 is a mobile telephone device (such as a smartphone) with a display for displaying graphical elements representative of liquid/food consumption. The second mobile computing device 550 is a mobile computer such as a Laptop or Tablet computer with a display for displaying graphical elements representative of liquid/food consumption.

The data processing system 530 is adapted to communicate output signals to the first 540 and second 550 mobile computing devices via the internet 520 (using a wired or wireless connection for example). As mentioned above, this may be undertaken in response to receiving a request from the first 540 or second 550 mobile computing devices.

Based on the received output signals, the first 540 and second 550 mobile computing devices are adapted to display one or more graphical elements in a display area provided by their respective display. For this purpose, the first 540 and second 550 mobile computing devices each comprise a software application for processing, decrypting and/or interpreting received output signals in order to determine how to display graphical elements. Thus, the first 540 and second 550 mobile computing devices each comprise a processing arrangement adapted to one or more values representative of liquid/food consumption, and to generate a display control signal for modifying at least one of the size, shape, position, orientation, pulsation or colour of the graphical element based on the one or more values representative of liquid/food consumption.

The system can therefore communicate information about inferred or detected liquid/food consumption to users of the first 540 and second 550 mobile computing devices. For example, each of the first 540 and second 550 mobile computing devices may be used to display graphical elements to a medical practitioner, a caregiver, a family member or close relative.

Implementations of the system of FIG. 5 may vary between: (i) a situation where the data processing system 530 communicates display-ready liquid/food consumption data, which may for example comprise display data including graphical elements (e.g. in JPEG or other image formats) that are simply displayed to a user of a mobile computing device using conventional image or webpage display (which can be web based browser etc.); to (ii) a situation where the data processing system 530 communicates raw data set information that the receiving mobile computing device then processes to determine one or more values representative of liquid/food consumption, and then displays graphical elements based on the determined one or more values (for example, using local software running on the mobile computing device). Of course, in other implementations, the processing may be shared between the data processing system 530 and a receiving mobile computing device such that part of the data generated at data processing system 530 is sent to the mobile computing device for further processing by local dedicated software of the mobile computing device. Embodiments may therefore employ server-side processing, client-side processing, or any combination thereof.

Further, where the data processing system 530 does not 'push' information (e.g. output signals), but rather communicates information in response to receiving a request, the user of a device making such a request may be required to confirm or authenticate their identity and/or security credentials in order for the information to be communicated.

Figure 6:
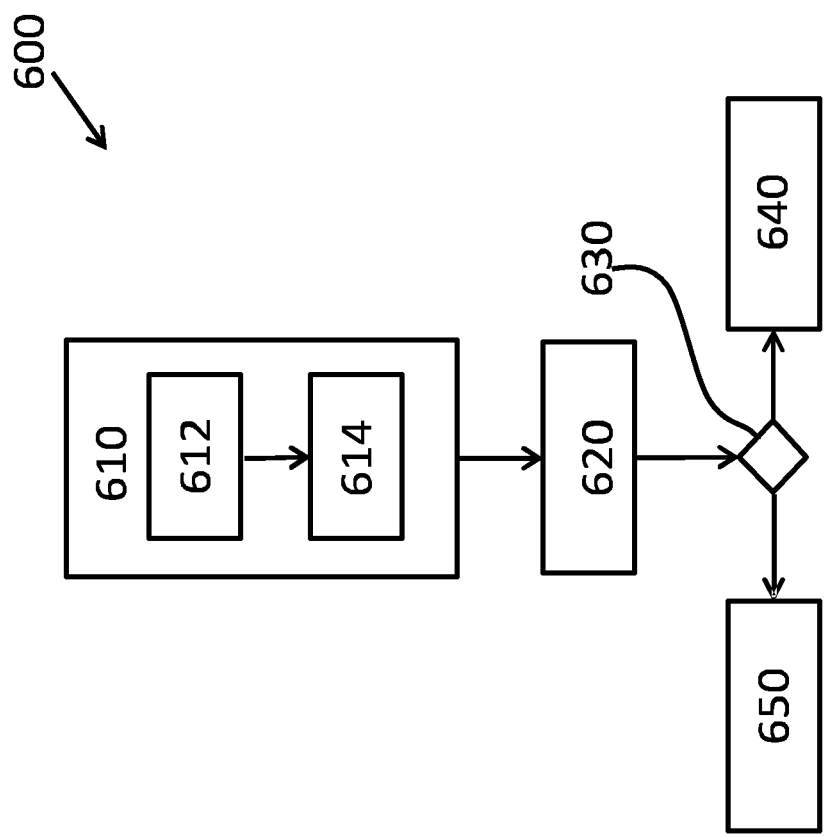
FIG. 6 shows a flow diagram of a method for monitoring the liquid or food consumption of a person according to an embodiment.

Referring now to FIG. 6, there is shown a flow diagram of a method 600 for monitoring the liquid or food consumption of a person.

The method begins with step 610 in which a change in weight of the person resultant from usage of a toilet is determined. Specifically, the step 610 of determining a change in weight of the person comprises the sub-steps of: detecting 612 the weight of the person before and after a single usage of the toilet; and determining 614 the change in weight of the person based on the detected weight of the person before and after the single usage of the toilet.

Next, in step 620, a value representative of at least one of liquid consumption and food consumption of the person is determined based on the detected change in weight of the person. Here, the step 620 of generating a value representative of at least one of liquid consumption and food consumption of the person is further based on: a value representative of weight lost by perspiration of the person; and a value representative of weight stored by the person. More specifically, the value (Win) representative of at least one of liquid consumption and food consumption of the person is obtained using the following equation (i):

$$Win=Wst+Wex+Wil \qquad (i),$$

wherein Wst is a value representative of weight stored by the person, Wex is the determined change in weight of the person, and Wil is a value representative of weight lost by perspiration of the person.

Then, in step 630, the determined value (Win) representative of at least one of liquid consumption and food consumption is compared with a predetermined threshold value. The threshold value can be preprogramed, fixed or dynamically set in response to calculations based on one or more previously obtained values (e.g. using trend analysis), but is preferably also enabled to be set by a user preference. Thus, the threshold may be based on previously determined values representative of liquid/food consumption of the person. In other words, the threshold may be defined by taking account of a history of liquid/food consumption of the person and/or taking account of previous calculations so that it can be used to identify outlying values or anomalies. Other methods to detect outliers or to detect changes in a time series are known in the art.

If, in step 630, the value (Win) representative of at least one of liquid consumption and food consumption is determined to exceed the first threshold value, the method proceeds to step 640 wherein a warning signal is generated and output along with the value (Win) representative of at least one of liquid consumption and food. If, in step 630, the value (Win) representative of at least one of liquid consumption and food consumption is determined to not exceed the first threshold value, the method proceeds to step 650 wherein the value (Win) representative of at least one of liquid consumption and food is output without any warning signal.

Thus, by way of example, by way of example, one or more steps of the method 600 for monitoring the liquid or food consumption of a person may be implemented in a portable computing device (such as the smartphone or portable computer shown in FIG. 5) in order to control the display of graphical elements on a display.

Figure 7:
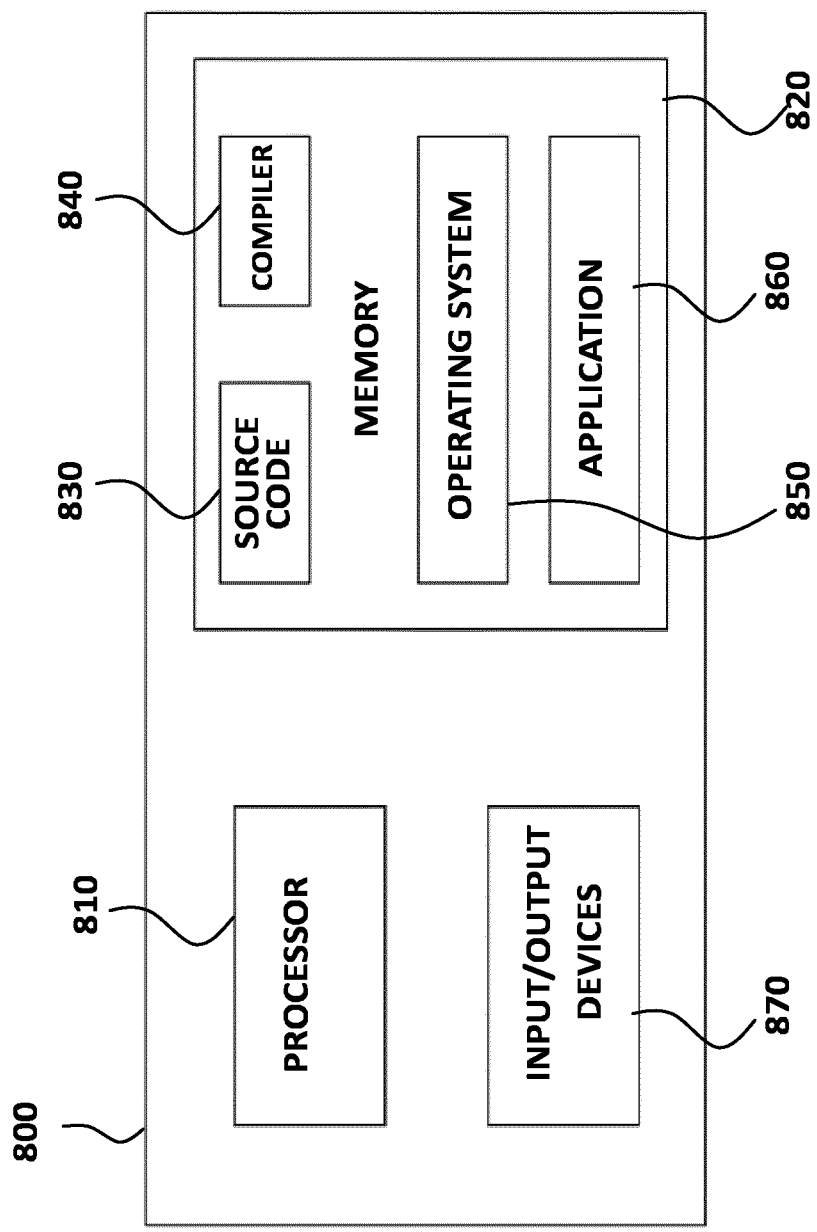
FIG. 7 is a simplified block diagram of a computer within which one or more parts of an embodiment may be employed.

FIG. 7 illustrates an example of a computer 800 within which one or more parts of an embodiment may be employed. Various operations discussed above may utilize the capabilities of the computer 800. For example, one or more parts of an ADL monitoring system for monitoring the liquid or food consumption of a person may be incorporated in any element, module, application, and/or component discussed herein.

The computer 800 includes, but is not limited to, PCs, workstations, laptops, PDAs, palm devices, servers, storages, and the like. Generally, in terms of hardware architecture, the computer 800 may include one or more processors 810, memory 820, and one or more I/O devices 870 that are communicatively coupled via a local interface (not shown). The local interface can be, for example but not limited to, one or more buses or other wired or wireless connections, as is known in the art. The local interface may have additional elements, such as controllers, buffers (caches), drivers, repeaters, and receivers, to enable communications. Further, the local interface may include address, control, and/or data connections to enable appropriate communications among the aforementioned components.

The processor 810 is a hardware device for executing software that can be stored in the memory 820. The processor 810 can be virtually any custom made or commercially available processor, a central processing unit (CPU), a digital signal processor (DSP), or an auxiliary processor among several processors associated with the computer 800, and the processor 810 may be a semiconductor based microprocessor (in the form of a microchip) or a microprocessor.

The memory 820 can include any one or combination of volatile memory elements (e.g., random access memory (RAM), such as dynamic random access memory (DRAM), static random access memory (SRAM), etc.) and non-volatile memory elements (e.g., ROM, erasable programmable read only memory (EPROM), electronically erasable programmable read only memory (EEPROM), programmable read only memory (PROM), tape, compact disc read only memory (CD-ROM), disk, diskette, cartridge, cassette or the like, etc.). Moreover, the memory 820 may incorporate electronic, magnetic, optical, and/or other types of storage media. Note that the memory 820 can have a distributed architecture, where various components are situated remote from one another, but can be accessed by the processor 810.

The software in the memory 820 may include one or more separate programs, each of which comprises an ordered listing of executable instructions for implementing logical functions. The software in the memory 820 includes a suitable operating system (O/S) 850, compiler 840, source code 830, and one or more applications 860 in accordance with exemplary embodiments. As illustrated, the application 860 comprises numerous functional components for implementing the features and operations of the exemplary embodiments. The application 860 of the computer 800 may represent various applications, computational units, logic, functional units, processes, operations, virtual entities, and/or modules in accordance with exemplary embodiments, but the application 860 is not meant to be a limitation.

The operating system 850 controls the execution of other computer programs, and provides scheduling, input-output control, file and data management, memory management, and communication control and related services. It is contemplated by the inventors that the application 860 for implementing exemplary embodiments may be applicable on all commercially available operating systems.

Application 860 may be a source program, executable program (object code), script, or any other entity comprising a set of instructions to be performed. When a source program, then the program is usually translated via a compiler (such as the compiler 840), assembler, interpreter, or the like, which may or may not be included within the memory 820, so as to operate properly in connection with the O/S 850. Furthermore, the application 860 can be written as an object oriented programming language, which has classes of data and methods, or a procedure programming language, which has routines, subroutines, and/or functions, for example but not limited to, C, C++, C#, Pascal, BASIC, API calls, HTML, XHTML, XML, ASP scripts, JavaScript, FORTRAN, COBOL, Perl, Java, ADA, .NET, and the like.

The I/O devices 870 may include input devices such as, for example but not limited to, a mouse, keyboard, scanner, microphone, camera, etc. Furthermore, the I/O devices 870 may also include output devices, for example but not limited to a printer, display, etc. Finally, the I/O devices 870 may further include devices that communicate both inputs and outputs, for instance but not limited to, a NIC or modulator/demodulator (for accessing remote devices, other files, devices, systems, or a network), a radio frequency (RF) or other transceiver, a telephonic interface, a bridge, a router, etc. The I/O devices 870 also include components for communicating over various networks, such as the Internet or intranet.

If the computer 800 is a PC, workstation, intelligent device or the like, the software in the memory 820 may further include a basic input output system (BIOS) (omitted for simplicity). The BIOS is a set of essential software routines that initialize and test hardware at startup, start the O/S 850, and support the transfer of data among the hardware devices. The BIOS is stored in some type of read-only-memory, such as ROM, PROM, EPROM, EEPROM or the like, so that the BIOS can be executed when the computer 800 is activated.

When the computer 800 is in operation, the processor 810 is configured to execute software stored within the memory 820, to communicate data to and from the memory 820, and to generally control operations of the computer 800 pursuant to the software. The application 860 and the O/S 850 are read, in whole or in part, by the processor 810, perhaps buffered within the processor 810, and then executed.

When the application 860 is implemented in software it should be noted that the application 860 can be stored on virtually any computer readable medium for use by or in connection with any computer related system or method. In the context of this document, a computer readable medium may be an electronic, magnetic, optical, or other physical device or means that can contain or store a computer program for use by or in connection with a computer related system or method.

The application 860 can be embodied in any computer-readable medium for use by or in connection with an instruction execution system, apparatus, or device, such as a computer-based system, processor-containing system, or other system that can fetch the instructions from the instruction execution system, apparatus, or device and execute the instructions. In the context of this document, a "computer-readable medium" can be any means that can store, communicate, propagate, or transport the program for use by or in connection with the instruction execution system, apparatus, or device. The computer readable medium can be, for example but not limited to, an electronic, magnetic, optical, electromagnetic, infrared, or semiconductor system, apparatus, device, or propagation medium.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The description has been presented for purposes of illustration and description, and is not intended to be exhaustive or limited to the invention in the form disclosed. Many modifications and variations will be apparent to those of ordinary skill in the art. Embodiments have been chosen and described in order to best explain principles of proposed embodiments, practical application(s), and to enable others of ordinary skill in the art to understand various embodiments with various modifications are contemplated.

The invention claimed is:

1. A method for monitoring the liquid and/or food consumption of a person with a computer system, the computer system comprising a processor, wherein the method comprises:

automatically receiving, by the computer system and from a sensor, values corresponding to a weight of a person before and after the use of a toilet;

automatically detecting, using the computer system, a change in weight of the person resultant from the person's use of a toilet; and determining, using the computer system, a value representative of at least one of the liquid consumption and the food consumption based on the detected change in weight of the person.

2. The method of claim 1, wherein the step of determining a value representative of at least one of liquid consumption and food consumption of the person is further based on at least one of:

a value representative of weight lost by perspiration of the person;

a value representative of weight lost by respiration of the person;

a value representative of reference weight;

one or more previously detected values of weight of the person;

one or more previously detected changes in weight of the person; and one or more previously determined values representative of preceding liquid or food consumption of the person.

3. The method of claim 2, wherein the value representative of the at least one of the liquid consumption and the food consumption of the person is equal to, or is further based on the sum of:

the detected change in weight of the person resultant from the person's use of the toilet;

the value representative of the reference weight;

the value representative of weight lost by perspiration of the person.

4. The method of claim 2, further comprising:

comparing the determined value representative of the at least one of liquid consumption and the food consumption with a threshold value; and generating a warning signal based on the comparison result.

5. The method of claim 4, further comprising, before the step of comparing the determined value representative of the at least one liquid consumption and the food consumption, the step of determining the threshold value based on at least one of:

one or more previously determined values representative of preceding liquid or food consumption of the person;

one or more previously detected changes in weight of the person; and one or more previously detected values of weight of the person.

6. The method of claim 1 wherein the step of automatically detecting a change of weight of the person resultant from the person's use of the toilet comprises:

detecting a weight of the person before and after a single usage of the toilet.

7. A computer program product for monitoring the liquid and/or food consumption of a person, wherein the computer program product comprises computer-readable program code stored on a computer-readable medium or downloadable from a communications network, which when executed by a processor, the computer-readable program code is configured to perform all of the steps of claim 1 when executed.

8. A system for monitoring the liquid and/or food consumption of a person, wherein the system comprises:

a data processing unit adapted to:

automatically receive values corresponding to a weight of a person before and after the use of a toilet;
automatically detect a change in weight of the person resultant from the person's use of a toilet; and
determine a value (Win) representative of at least one of the liquid consumption and the food consumption of the person based on the detected change in weight of the person.

9. The system of claim 8, wherein the data processing unit is further adapted to determine the value representative of at least one of the liquid consumption and the food consumption of the person further based on at least one of:
a value representative of weight lost by perspiration of the person;
a value representative of weight lost by respiration of the person;
a value representative of a reference weight;
one or more previously detected values of weight of the person;
one or more previously detected changes in weight of the person; and
one or more previously determined values representative of preceding liquid or food consumption of the person.

10. The system of claim 9, wherein the data processing unit is further adapted to determine the value representative of the at least one of the liquid consumption and the food consumption of the person as equal to, or as further based on the sum of:
the detected change in weight of the person resultant from the person's use of the toilet;
the value representative of the reference weight;
the value representative of weight lost by perspiration of the person.

11. The system of claim 8, wherein the data processing unit is further adapted to:
compare the determined value representative of at least one of the liquid consumption and the food consumption with a threshold value; and
to generate a warning signal based on the result of the comparison.

12. The system of claim 11, wherein the threshold value is determined based on at least one of:
one or more previously determined values representative of preceding liquid or food consumption of the person;
one or more previously detected changes in weight of the person; and
one or more previously detected values of weight of the person.

13. The system of claim 8, further comprising a weight sensing system adapted to:
detect a weight of the person before and after a single usage of the toilet and to determine data related to the change in weight of the person resultant from the person's use of the toilet based on the detected weight of the person before and after the single usage of the toilet.

14. The system of claim 13, wherein the weight sensing system is adapted to:
be part of the toilet such that it is capable of detecting the weight of a person when the person is sitting on the toilet before and after the person's usage, or
be positioned in front of the toilet so that it is stood on by the person before and after the person's usage of the toilet.

15. A system for monitoring the liquid and/or food consumption of a person, wherein the system comprises:
a data processing unit adapted to:
automatically detect a change in weight of the person resultant from the person's use of a toilet; and
determine a value (Win) representative of at least one of the liquid consumption and the food consumption of the person based on the detected change in weight of the person; and
a server device for communication with a remote client device including a weight sensing system as defined in claim 13, wherein the server device comprises:
a communication link for receiving data related to a detected change in weight of the person resultant from the person's use of the toilet from the client device, the data being suitable for the data processing unit to provide or obtain the current value representative of the change in weight of the person.

16. The system of claim 15 comprising the client device, wherein the client device comprises:
a communication link for transmitting the data related to a change in weight of the person resultant from usage of a toilet by the person resultant from the person's use of the toilet.

17. The system of claim 8, comprising a client device, for communication with a server device, wherein the client device comprises:
the data processing unit; and
a communication link for transmitting the value representative of at least one of the liquid consumption and the food consumption of the person.

18. The system of claim 17 comprising the server device, wherein the server device comprises a communication link for receiving the value representative of at least one of the liquid consumption and the food consumption of the person.

19. The system of claim 8, comprising a further data processing unit adapted to generate a control signal for a display device, the control signal comprising instructions for displaying a graphical element that represents the determined value representative of the at least one of the liquid consumption and the food consumption of the person.

20. A method for monitoring the liquid and/or food consumption of a person with a computer system, the computer system comprising a processor, wherein the method comprises:
automatically receiving, by the computer system and from a sensor, values corresponding to a weight of a person before and after the use of a toilet;
automatically detecting, using the computer system, a change in weight of the person resultant from the person's use of a toilet;
determining, using the computer system, a reference weight of the person and a value representative of weight lost by respiration and perspiration of the person;
determining, using the computer system, a value representative of at least one of the liquid consumption and the food consumption based on the detected change in weight, the reference weight and the value representative of weight lost by respiration and perspiration of the person; and
generating, using the computer system, a control signal for a display device, the control signal including instructions for displaying a graphical element that represents the determined value representative of the at least one of the liquid consumption and the food consumption of the person.

21. The method of claim 20, wherein the value representative of weight lost by respiration and perspiration of the person is determined based on a body size of the person and environmental conditions of an environment associated with the person.

22. The method of claim 20, wherein automatically receiving the values corresponding to the weight of the person includes:
- receiving a signal from a location sensor associated with the person,
- determining, based on the signal, the person is located near the toilet, and
- confirming, based on the determining, the received values correspond to the person.

* * * * *